United States Patent [19]

White

[11] 4,214,874
[45] Jul. 29, 1980

[54] COMBINATION AND METHOD FOR MIXING THE CONTENTS OF A BLOOD COLLECTION TUBE AND THEREAFTER REMOVING THE MIXING ELEMENT

[75] Inventor: Fred K. White, Miami, Fla.
[73] Assignee: American Hospital Supply Corporation, Evanston, Ill.
[21] Appl. No.: 10,234
[22] Filed: Feb. 8, 1979
[51] Int. Cl.² ............... G01N 33/16; B01F 13/08
[52] U.S. Cl. ............... 23/230 B; 73/425.4 P; 220/352; 220/DIG. 19; 366/273; 422/100
[58] Field of Search ............... 23/230 B; 422/99, 100; 366/243, 273, 332, 344, 348; 73/421 R, 425.4 P; 220/DIG. 19, 352; 128/1.3

[56] References Cited
U.S. PATENT DOCUMENTS

| | | | |
|---|---|---|---|
| 3,219,318 | 11/1965 | Hershler | 366/273 |
| 3,784,170 | 1/1974 | Petersen et al. | 366/273 |
| 3,985,649 | 10/1976 | Eddelman | 366/273 X |

*Primary Examiner*—Arnold Turk
*Attorney, Agent, or Firm*—Tilton, Fallon, Lungmus & Chestnut

[57] ABSTRACT

Combination and method for mixing a blood sample and an anticoagulant within a collection tube and for then capturing, removing and discarding the mixing element without danger of direct contact between the blood sample and the technician. The full combination includes a blood collection tube, at least one resilient end cap for the tube having a cavity which extends well beyond that tube when the cap is in place, a magnetic element slidable within the tube and receivable in the cap, and a magnet for shifting the magnetic element. After being directed into the cap following a mixing operation, the blood-covered magnetic element may be held within the cavity by finger pressure on the cap and discarded along with the cap.

19 Claims, 10 Drawing Figures

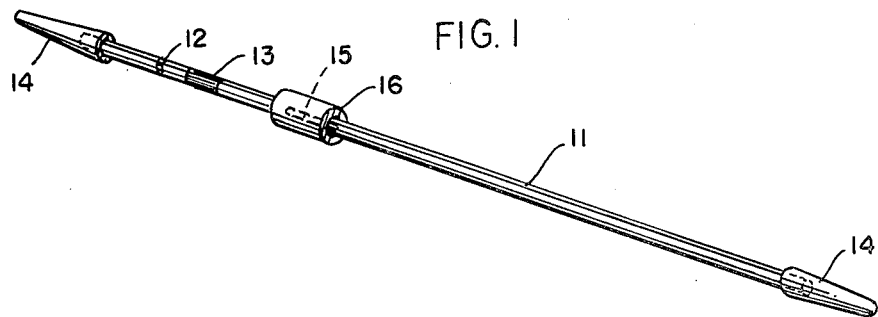
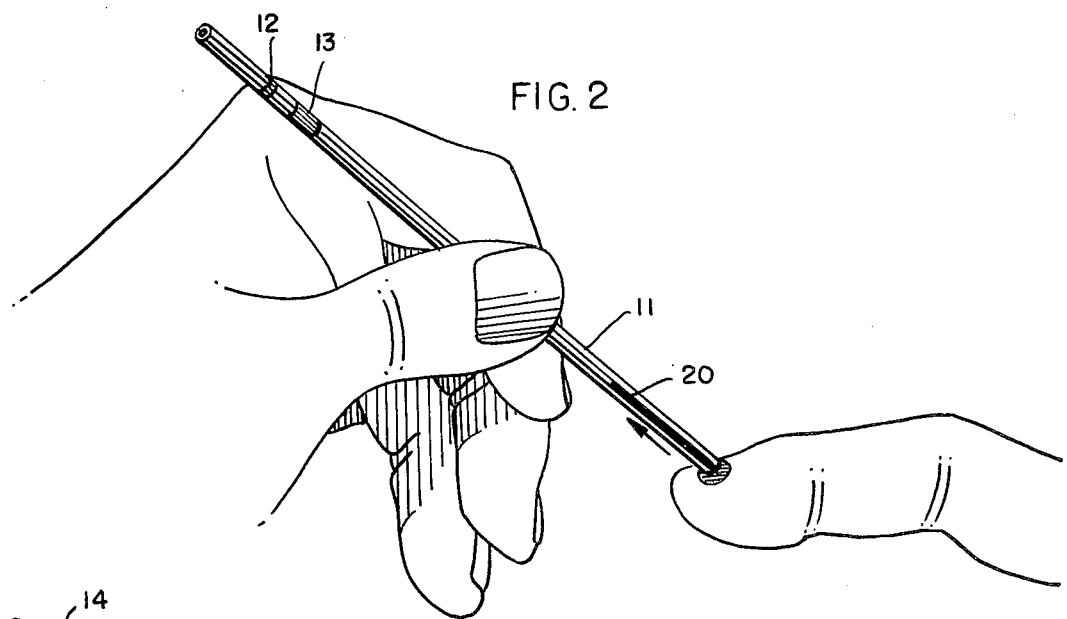
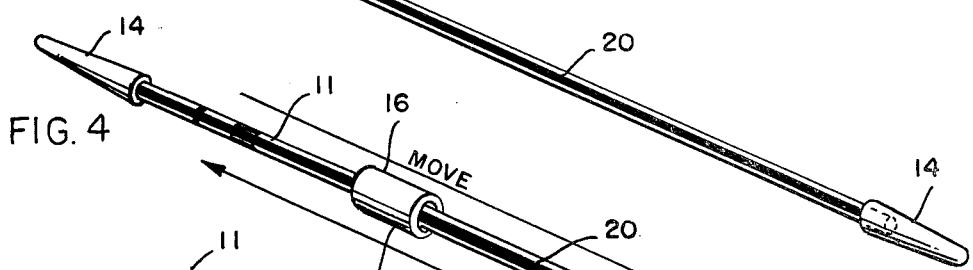
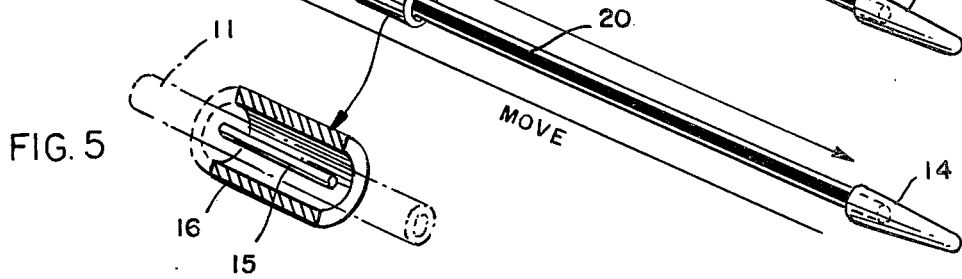

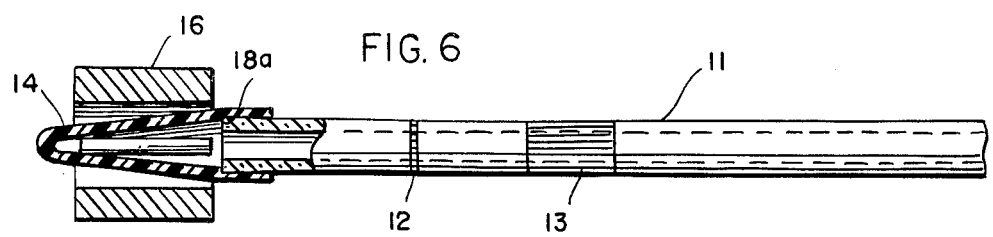
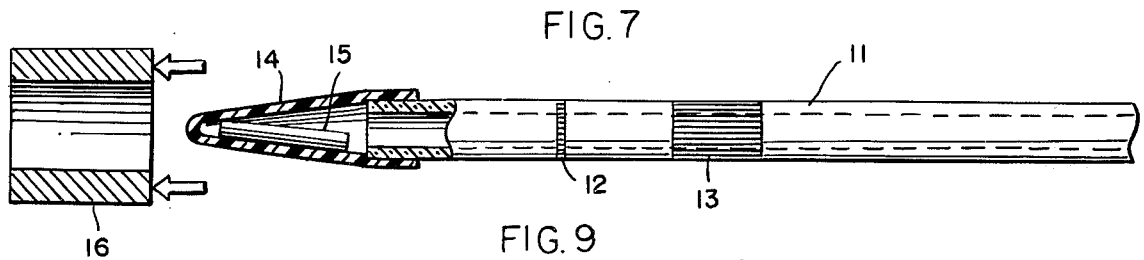
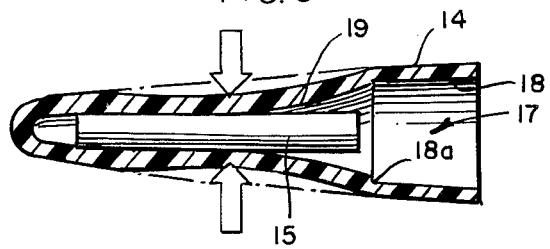
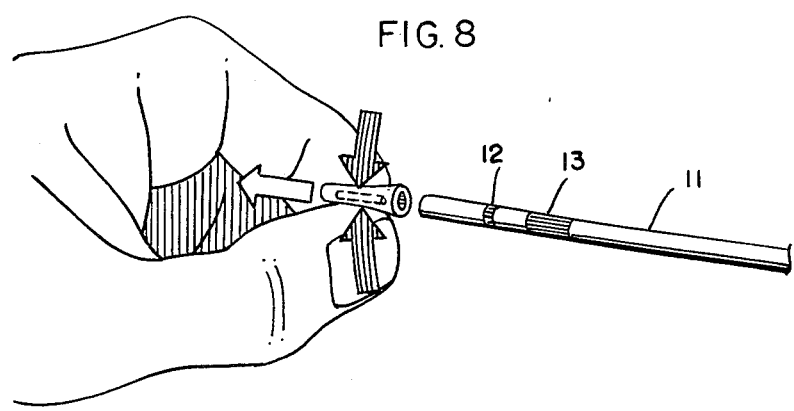
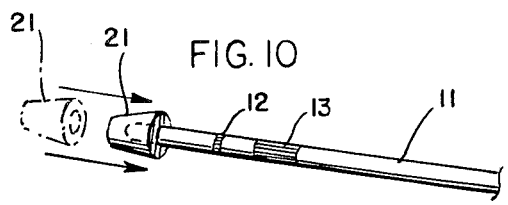

COMBINATION AND METHOD FOR MIXING THE CONTENTS OF A BLOOD COLLECTION TUBE AND THEREAFTER REMOVING THE MIXING ELEMENT

BACKGROUND AND SUMMARY

It has been known in the past to utilize small magnetic elements to mix blood drawn into collection tubes for clinical testing with an anticoagulant, normally a heparin salt, which coats the interior surfaces of the tubes. The ferromagnetic element or slug is simply inserted into the bore of the tube after a blood sample has been taken and the element is then shifted back and forth within the tube under the direction of an external magnet manipulated by the technician. Following such a mixing operation, the magnetic element is extracted from the tube by means of the magnet, and is then separated from the magnet and discarded or washed for re-use. Danger lies in the fact that considerable difficulty is often encountered in performing such steps without direct contact between the sample blood and the technician's fingers. Such contact is practically inevitable if the magnet and/or the mixing element are to be washed and re-used. Since the blood may indeed have one or more of the pathological conditions for which it is intended to be tested, and since at least some of those conditions are highly infectious (serum hepatitis, for example), it is apparent that any direct contact between the user and the sample blood involves serious risks and should be avoided. Despite such risks, an effective and dependable solution to these problems has been wanting.

In view of the difficulties involved in removing the blood-coated magnetic elements from such collection tubes or in separating the contaminated elements from the reusable magnets, without risking direct finger contact with the sample blood, some users either omit the magnetic mixing step completely or leave the magnetic elements within the collection tubes following the mixing step. Should the mixing step be completely omitted, the sample blood may become coagulated and either preclude proper testing or render the results meaningless or misleading. On the other hand, should a magnetic element be left within a collection tube, whether accidentally or intentionally, the ferromagnetic element is likely to be drawn into and obstruct the flow circuit of an automatic analyzer, possibly causing serious damage to its intricate system and requiring costly, time-consuming repairs.

This invention involves the discovery of a relatively simple but highly effective solution to such problems. All of the advantages of the magnetic mixing procedure may be realized without the risks of contamination previously associated with that procedure. Specifically, by the method and combination of this invention it is now possible to perform magnetic mixing in a blood collection tube and thereafter capture, remove, and discard the magnetic slug or mixing element without danger of direct contact between the blood sample and a user's fingers.

Briefly, the system involves the use of at least one elongated tubular cap as the means for sealing one (or both) ends of a blood collection tube. In the best form known for practicing the invention, such a cap should be resilient and be provided with an elongated tapered cavity having a mouth portion for snugly but removably receiving an end of the collection tube and having a main cavity portion extending beyond that tube when the cap is in place. The length and diameter of the interior of the cap exceed the corresponding dimensions of the magnetic element or slug used for mixing blood and anticoagulant within the collection tube. However, once the magnetic element is fully received within the cap, the opposite wall portions of that cap may be squeezed together by the user's fingers to hold the magnetic element within the cavity of the cap. Without changing the positions of his fingers, the user then simply detaches the cap from the collection tube and, with the blood-coated collection tube captured within the cavity, the cap and magnetic elements are discarded together. Since the cap initially forms a fluid-tight seal with the collection tube, and since that seal is not disturbed until after the blood-coated magnetic element is fully received within the cavity of the cap and securely held in place therein, the dangers of direct contact between the sample blood and the technician's fingers during such an operation are eliminated or at least greatly reduced.

Other advantages, features, and objects of the invention will become apparent from the specification and drawings.

DRAWINGS

FIG. 1 is a perspective view of a blood collecting tube, end caps, mixing element, and magnet adapted for use in practicing the present invention.

FIG. 2 is a perspective view illustrating a blood collecting step.

FIG. 3 illustrates the tube following blood collection and prior to insertion of the magnetic mixing element.

FIGS. 4 and 5 depict the mixing step and the relationship of the operative components during such step.

FIGS. 6 and 7 are fragmentary side elevational views shown partly in section and depicting the step of shifting the magnetic mixing element into the cavity of an end cap.

FIG. 8 is a perspective view illustrating the step of removing the end cap and captured mixing element from the collecting tube.

FIG. 9 is an enlarged sectional view illustrating the retention of the mixing element within the removed end cap.

FIG. 10 is a perspective view illustrating the resealing of the end of the tube from which the mixing element has been withdrawn.

DESCRIPTION OF PREFERRED EMBODIMENT

Referring to the drawings, the numeral 11 designates a standard micropipet of the type commonly used for blood collection. Such pipets or tubes are commonly formed of glass and are available in a variety of sizes and volumetric capacities. For example, in microchemistry procedures tubes having a measured sample capacity of about 0.1 milliliter (ml) or 100 microliters ($\mu$l) are used, whereas in ultramicro procedures the measured volumetric capacities are about 0.01 ml (10 $\mu$l), and for macro procedures, about 1.0 ml (1000 $\mu$l). Thus, depending on the particular tests to be conducted and the preferences of the technicians conducting such tests, the blood collecting tubes may have measured volumetric capacities ranging from just a few microliters to one or more milliliters, although a more typical range would be from about 5 to 100 microliters. Such tubes are precision manufactured and calibrated to accuracies commonly within plus or minus one half percent, a typical calibration mark 12 being represented in the drawings. Another mark 13 is conventionally used to represent whether the tube is or is not internally coated with an anticoagulant, such as a heparin salt, a blue color-coated band indicating the absence of such anticoagulant coating and a red band indicating that such a coating is present. Since the present invention is concerned with problems associated with the mixing of blood with anticoagulant, the tube 11 used in connection with this invention would ordinarily be precoated with anticoagulant by the manufacturer. It is to be understood, however, that in some instances the technician might introduce the anticoagulant into the tube just prior to the blood-drawing step, as in a procedure where a measured amount of dilute sodium oxalate is first drawn into the tube by the technician.

Tube 11 is shown in FIG. 1 with end caps 14 fitted upon its opposite ends. As will be described hereinafter, collection procedures require that opposite ends of such a tube be sealed following the blood collecting step. In the past, such sealing has commonly been achieved by inserting the ends of the pipet into a wax-like sealant, although end caps differing from the caps 14 disclosed herein have also been used for that purpose. It is to be noted that while two identical end caps 14, each of distinctive structure, are shown in the drawings, this invention may be practiced using only one such end cap 14, the other end of the tube being sealed by a conventional sealant plug or other type of closure.

The complete assembly also includes a ferromagnetic element or slug 15, shown in FIG. 1 within the bore of collection tube 11, and a magnet 16 disposed externally of the collection tube. Preferably the magnet 16 is annular in configuration with an inside diameter substantially larger than the outside diameter of the collection tube.

End cap 14 defines an elongated cavity 17, the cavity having a mouth portion 18 which sealingly receives the end of the collection tube 11 and a main cavity portion 19 extending well beyond the end of that tube. An annular shoulder 18a is preferably located between the two cavity portions to provide a stop for limiting the extent of insertion of tube 11 (FIG. 9). As shown in FIGS. 6 and 7, the smallest diameter of the shoulder is larger than the inside diameter of the collection tube so that the shoulder will not restrain sliding movement of the magnetic element 15 from tube 11 into cap 14. The composite cavity 17 is gradually tapered as shown and is substantially longer than the rod-like ferromagnetic element 15. Consequently, element 15 is capable of being completely received within cavity 17 and, preferably, within the main portion 19 of that cavity.

The cap may be formed from any suitable resilient and flexible material. Particularly effective results have been obtained with polymers of ethyl vinyl acetate (one suitable brand being available under the designation EVA 3180 from E. I. duPont deNemours, Wilmington, Del.), although other flexible plastics having similar properties might be used. Such flexibility is particularly advantageous for the purpose of allowing opposite side wall portions of the cap to be urged inwardly by finger pressure so as to cause such wall portions to engage the magnetic element 15 and to hold that element securely within the cavity of the cap (FIGS. 8 and 9).

It is also highly advantageous for the cap 14 to be formed of a plastic which is transparent, thereby permitting the magnetic element to be viewed through the side wall of the cap when that element is received within cavity 17. The term "transparent" as used herein is therefore intended to mean any material which transmits enough light to allow such verification, even though the material might generally be regarded as milky, tinted, or transparent.

The annular magnet 16 is of conventional construction although, for purposes of this invention, it is important that the inside diameter of that magnet be substantially larger than the maximum outside diameter of the tapered cap 14. Hence, the magnet may be easily slipped off of the end of the collection tube without disturbing cap 14 (FIG. 7).

In carrying out the method of this invention, the user draws a blood sample from a patient in the conventional manner depicted in FIG. 2, the blood 20 entering the bore of the tube by reason of capillary attraction either with or without the assistance of a conventional suction tube. After drawing the sample to calibration mark 12, the technician inserts the magnetic mixing element 15 into the tube and then seals the ends of the tube, at least one such end being sealed by a tapered cap 14. Magnet 16 is then shifted alternately in opposite directions along the length of the tube to mix the blood sample with the anticoagulant originally present in the tube. Where the anticoagulant takes the form of a heparin coating along the inside surface of the tube, the mixing elements acts to scrape that coating from the interior surfaces and to mix it throughly with the blood sample.

Thereafter, the technician moves magnet 16 beyond the end of the tube closed by cap 14. As the magnet is slipped over and beyond the cap, the magnetic element 15 is drawn within the cavity 17 (FIG. 7). The presence of the magnet within the cavity may be checked visually because of the general transparency of the cap. Tactile verification may also be undertaken by squeezing the cap and detecting whether the inwardly flexed side wall engages the metallic element 15. Thereafter, the user simply removes the cap and magnet from the collection tube, squeezing the cap as indicated in FIGS. 8 and 9 to insure that the captured magnetic element is retained within the cap. The cap 14 and magnetic element 15 are then discarded into a suitable bio-hazard receptacle, and the end of the tube is resealed in any appropriate manner. As shown in FIG. 10, a closure 21 may be fitted upon the end of the tube or, if desired, the end of the tube may be closed by a suitable sealant material using procedures well known in the art.

It is to be noted that cap 14 performs the dual functions of sealing the end of tube 11 during a mixing operation and of serving as a receptacle for capturing, removing, and discarding the blood-coated mixing element 15. Since the inner surface of the cap defining the mouth portion 18 of the cavity sealingly engages the outer surface of the collection tube 11 prior to removal of the cap, and since the magnetic element 15 is secured within the main portion 19 of the cavity before the cap is disengaged from the tube, it is unlikely that any blood will appear at the mouth of the cavity after separation of the tube and cap has taken place. Also, it will be noted that the user's fingers would be spaced away from the open end of the cap if the fingers were properly placed for the most effective squeezing action in securing the magnetic element within the cavity and for removing the cap without at the same time increasing resistance to withdrawal of that cap from the tube. As a result, the magnetic element, coated with residual blood, may be safely removed from tube 11 without danger of direct contact between the user's fingers and such blood.

Magnet 16 remains free of blood and may, if desired, be reused. The problems associated with prior procedures, in which such a magnet when withdrawn from the collection tube carries with it the blood-coated magnetic element, and such magnet must thereafter be washed free of blood if it is to be reused, are therefore completely avoided.

While in the foregoing I have disclosed an embodiment of the invention in considerable detail for purposes of illustration, it will be understood by those skilled in the art that many of these details may be varied without departing from the spirit and scope of the invention.

I claim:

1. A method for mixing blood with anticoagulant in a collection tube and thereafter safely removing the mixing element therefrom, said method involving the preliminary steps of drawing blood into a collection tube containing anticoagulant, introducing a magnetic element into said tube, sealing the ends of the tube, and thereafter moving a magnet back and forth along the outside of the tube to shift the magnetic element within the tube and thereby mix the blood and anticoagulant together, wherein the improvement comprises utilizing an elongated tubular resilient cap as the means for sealing at least one end of said tube, said cap providing an elongated cavity having a mouth portion sealingly and removably receiving an end of said tube and having a main cavity portion extending beyond said tube, moving said magnet to shift said element into said cavity of said cap after said blood and anticoagulant have been mixed in said tube, and thereafter removing and discarding said cap with the blood-coated magnetic element captured therein.

2. The method of claim 1 in which the combined length of said mouth portion and said main portion of said cavity is substantially greater than the length of said magnetic element.

3. The method of claims 1 or 2 in which said step of removing said cap is accompanied by the further step of squeezing the portion of said cap extending beyond said tube between the user's fingers so that said magnetic element is gripped and held between interior surface portions of said cap.

4. The method of claims 1 or 2 in which said magnet is annular and is loosely fitted about said tube for shifting said magnet during said mixing step, said step of moving said magnet to shift said element into the cavity of said cap including the step of moving said annular magnet off of said tube and axially away from said cap.

5. A method for mixing blood with anticoagulant in a blood collection tube and thereafter safely removing the mixing element from that tube, said method involving the preliminary steps of drawing blood into a standard blood collection tube containing anticoagulant, introducing a magnetic element into said tube, sealing the ends of said tube, and thereafter loosely fitting an annular magnet over said tube and moving said magnet back and forth along the length of said tube to shift said magnetic element within the tube and to mix the blood and anticoagulant therein, wherein the improvement comprises utilizing an elongated tubular resilient cap as the means for sealing at least one end of said tube, said cap providing an elongated cavity having a mouth portion receivng said one end of said tube and having a main portion extending beyond said one end of said tube, moving said magnet off of said one end of said tube and away from said cap to shift said magentic element into the cavity of said cap after said blood and anticoagulant have been mixed together, squeezing the portion of said cap extending beyond said one end of said tube to hold said magnetic element within said cavity, and thereafter removing said cap and said magnetic element held therein from said tube and discarding said cap and the magnetic element captured therein.

6. A combination for mixing blood in a collection tube and for then removing and discarding the mixing element without danger of direct blood contact with the user, comprising an elongated blood collection tube having a bore for receiving a blood sample, means for sealing the ends of said tube, said means including a cap providing an elongated cavity having a mouth portion removably receiving one end of said tube and a main portion adapted to extend beyond said one end of said tube, a magnetic element slidable within said tube and dimensioned to be received within the cavity of said cap, and a magnet adapted to be moved along the outside of said tube for mixing the contents thereof and for thereafter shifting said magnetic element into said cap, whereby, said cap with said magnet captured therein may be removed and discarded without direct contact between the user and the contents of the tube.

7. The combination of claim 6 in which said magnetic element is rod-shaped and has a length substantially less than the length of said elongated cavity.

8. The combination of claim 6 in which said cavity of said cap is tapered.

9. The combination of claim 6 in which said magnet is annular and said cap has a maximum external diameter smaller than the inside diameter of said magnet.

10. The combination of claim 6 in which said cap is transparent.

11. The combination of claim 6 in which said cap includes an internal shoulder between said mouth portion and said main portion of said cavity, said shoulder being engageable with said one end of said tube to limit the insertion of said tube into said cavity.

12. The combination of claim 11 in which the smallest diameter of said shoulder is greater than the inside diameter of said collection tube.

13. The combination of claims 6, 7, 8, 9, 10, 11 or 12 in which said cap is formed of resilient plastic material, said cap having wall portions capable of being deformed inwardly when squeezed between a user's fingers to engage and retain the magnetic element within said cap as said cap is removed from said tube and discarded.

14. A combination for use in mixing blood and anticoagulant within a blood collection tube and for thereafter removing and discarding the mixing element without danger of direct contact between the blood and a user, comprising a resilient cap provided with an elongated cavity having a mouth portion for sealingly but removably receiving an end of a blood collection tube and having a main portion adapted to extend beyond the end of such tube, a magnetic element dimensioned to slide within a blood collection tube and to fit within said cavity of said cap, said resilient cap having wall portions extending about said main portion of said cavity capable of being flexed inwardly to engage and grip said magnetic element when said element is disposed within said cavity and said wall portions are squeezed between a user's fingers.

15. The combination of claim 14 in which said combination also includes an annular magnet for shifting said magnetic element through the bore of said tube and into said cap, said annular magnet having an inside diameter greater than the maximum outside diameter of said cap.

16. The combination of claims 14 or 15 in which said magnetic element is rod-shaped and has a length substantially less than the length of said elongated cavity.

17. The combination of claims 14 or 15 in which said cavity of said cap is tapered.

18. The combination of claim 14 in which said cap is transparent.

19. The combination of claim 14 in which said cap includes an internal shoulder between said mouth portion and said main portion of said cavity, said shoulder being adapted for engagement with the end of a blood collection to limit the extent of insertion of such tube into said cavity.

* * * * *